United States Patent [19]

Mimura et al.

[11] Patent Number: 4,760,021
[45] Date of Patent: Jul. 26, 1988

[54] BIOLOGICAL RESPONSE MODIFIER HAVING CELL DIFFERENTIATION-INDUCTION ACTIVITY AND PROCESS FOR PRODUCTION THEREOF

[75] Inventors: Akio Mimura; Kaoru Yoshinari; Katsumi Yuasa; Tsuneo Sato, all of Fuji, Japan

[73] Assignee: Director-General of Agency of Industrial Science & Technology, Tokyo, Japan

[21] Appl. No.: 668,904

[22] Filed: Nov. 7, 1984

[30] Foreign Application Priority Data

Nov. 14, 1983 [JP] Japan ................. 58-212436

[51] Int. Cl.$^4$ .............. C12P 21/00; C07K 3/02; A61K 37/02
[52] U.S. Cl. ......................... 435/68; 530/351
[58] Field of Search ............... 530/351; 435/68

[56] References Cited

PUBLICATIONS

Rovera et al., "Induction of Differentiation in Human Promyelocytic Leukemia Cells by Tumor Promotors", Science, vol. 204, 25 May 1979, pp. 868–870.
Olsson et al., "Characterization of Mononuclear Cell-Derived Differentiation Inducing Factors for the Human Promyelocytic Cell Line HL-60", JNCI, 67, 6 Dec. 1981, pp. 1225–1230.
Maeda et al., "Characterization of a Differentiation-Stimulating Factor for Mouse Myeloid Leukemia Cells", Gann, 68, Aug. 1977, pp. 435–447.
Vogel et al., "LPS unresponsive Mice as a Model for Analyzing Lymphokine-Induced Maerophage Differentiation in Vitro", Lymphokines 3, E. Pick and M. Landy Eds., Academic Press, New York, 1981, pp. 153–154.

William F. Ganong, "Review of Medical Physiology", Chapter 27, pp. 414–416.
Olsson et al., Cancer Research, 42, 3928–3933 (1982).
Tsuchiya et al., Int. J. Cancer, 26, 171–176 (1980).

Primary Examiner—John Tarcza
Attorney, Agent, or Firm—Birch, Stewart, Kolasch & Birch

[57] ABSTRACT

There is provided a proteinaceous biological response modifier having the following properties: (a) molecular weight: 35,000 to 65,000; (b) isoelectric point: 5.0 to 6.1; (c) physiological action on human leukemia cells: to induce human leukemia to differentiate into macrophage-like cells; (d) physiological action on myeloid leukemia cells from mice: to induce myeloid leukemia cells from mice to differentiate into macrophage-like cells; (e) affinity to Concanavalin A Sepharose: not adsorbed; (f) affinity to Blue Sepharose Resin: not adsorbed; (g) pH-stability and thermostability: substantially not inactivated at pH 2 to 10, at 2° C. for 6 hours; not inactivated at 56° C. for 60 minutes; but inactivated by 30% at 70° C. for 60 minutes; (h) sensitivity to enzymes: not inactivated by deoxyribonuclease; not inactivated by glycosidase; and inactivated by protease; (i) flow cytometry analysis: to concentrate cell division cycle of human leukemia cells to $G_0/G_1$ phase. There is also provided a process for the production of the proteinaceous biological response modifier comprising culturing human leukemia cells in a differentiation medium in the presence of a substance capable of inducing the human leukemia cells to differentiate into macrophage-like cells; separating the macrophage-like cells from the culture medium; activating the macrophage-like cells in a production medium by a mitogen to enhance the production of the proteinaceous biological response modifier; and isolating the proteinaceous biological response modifier from the production medium.

The biological response modifier has anti-tumor activity.

15 Claims, 4 Drawing Sheets

—●— : PRESENCE OF DAF
—○— : ABSENCE OF DAF

BIOLOGICAL RESPONSE MODIFIER HAVING CELL DIFFERENTIATION-INDUCTION ACTIVITY AND PROCESS FOR PRODUCTION THEREOF

BACKGROUND OF THE INVENTION

1. Field of the Invention

The present invention relates to a novel purified biological response modifier having cell differentiation-induction activity which is herein referred to as Differentiation and Activation Factor and abbreviated as DAF and a process for the production thereof.

2. Description of the Prior Art

A phenomenon of cell differentiation is a process where cells capable of division and growth change into functionally matured cells responsible for the functions of an organism. For example, the processes are well known where hematopoietic stem cells constantly differentiate into matured blood cells such as leukocytes, erythrocytes, monocytes and macrophages. This differentiation and maturation process is controlled by various kinds of biological response modifiers, resulting in maintenance of the homeostasis of an organism.

Conversely it is believed that leukemia cells are derived from hematopoietic stem cells, wherein the hematopoietic stem cells are tumorized into growing cells during the normal differentiation and maturation process of the stem cells.

If such leukemia cells could be induced to redifferentiate into cells having normal functions, a new therapy of leukemia could be established on the basis of the differentiation principle. It is from such a point of view that recently, in addition to the conventional chemotherapy, radiation therapy and immunotherapy, a new type of therapy which detumorizes cancer cells into normal cells by redifferentiation of the cancer cells, has been actively investigated.

Proteinaceous substances from mice which induce myeloid leukemia cells to differentiate and detumorize into macrophage-like cells were reported as a D-factor [*J. Cell. Physiol.*, 74, 223 (1969)]. The D-factors obtained from the culture of murine embryo cells are considered to be glycoprotein with a molecular weight of 40,000 to 50,000 [*Gann*, 68, 435 (1977)]. When a laboratory strain of myeloid leukemia cells from mice was implanted in a mouse and the D-factors derived from murine embryo cells were administered, the implanted myeloid leukemia cells were induced to redifferentiate into normal cells, and a life-prolongation effect on the mouse was observed [*Gan to Kagaku Ryoho*, Vol 8, No. 1, 8 (1981)]. Thus the literature as mentioned above suggests the possibility of cancer therapy with these differentiation-induction factors.

However, as the D-factors are proteinaceous substances derived from mice, they could cause an allergic response in a human body when administered. Therefore it is desirable to obtain a differentiation-induction factor derived from human stock. Proteinaceous differentiation-induction factors derived from human stock were produced by stimulation of the human peripheral lymphocyte with lectins, according to the *J. National Cancer Institute*, 67, 1225 (1981), *Cancer Research*, 42, 3928 (1982). However, none of the substantial properties of the differentiation-induction factors were described except that the factors were proteinaceous substances with a molecular weight of 25,000 and 40,000, as determined by gel filtration using Sephadex G-75 (Pharmacia Fine Chemicals A.B., Sweden).

Conversely differentiation-induction factors found in the supernatant of a culture of human T-cell leukemia cells were reported to be proteinaceous substances with a molecular weight of 50,000 to 60,000, as determined by acrylamide gel electrophoresis. The activity of the factors was lost by about 60% to 90% during the isolation procedures [Summary of Japan Tissue Culture Communication, 43, (1983)].

As described above, regarding the differentiation-induction factors derived from human peripheral lymphocytes and human T-cell leukemia cells, only the molecular weights have been reported and other properties of the factors have not been reported since these factors have not been obtained in an amount sufficient to allow the investigation of their properties.

As human peripheral lymphocytes can be obtained only from human blood, it is difficult to collect a large amount of the differentiation-induction factors from human peripheral lymphocytes and accordingly their industrial production is by no means easy. Also, since the maintenance of safety is expensive during the industrial culture of human T-cell leukemia cells which are infected with human T-cell leukemia virus (HTLV) and are proliferative, an economical production of the factors from human T-cell leukemia cells is very difficult.

On the other hand, macrophages are known to produce and secrete many kinds of biological response modifiers and are important for immune response. However, as human functional macrophages cannot be cultured, industrial production of these modifiers is also impossible.

Accordingly, it is desirable to establish a process for the production of a proteinaceous biological response modifier having differentiation-induction activity, wherein an established cell line capable of proliferating in vitro and not including a leukemia virus is used.

SUMMARY OF THE INVENTION

In accordance with the present invention, there is provided a new purified proteinaceous biological response modifier with differentiation-induction activity, having the following properties:

(a) molecular weight: 35,000 to 65,000;

(b) isoelectric point: 5.0 to 6.1;

(c) physiological action on human leukemia cells: to induce human leukemia to differentiate into macrophage-like cells;

(d) physiological action on myeloid leukemia cells from mice: to induce myeloid leukemia cells from mice to differentiate into macrophage-like cells;

(e) affinity to concanavalin A Sepharose: not adsorbed;

(f) affinity to Blue Sepharose resin: not adsorbed;

(g) pH-stability and thermostability: substantially not inactivated at pH 2 to 10, at 2° C. for 6 hours; not inactivated at 56° C. for 60 minutes; but inactivated by 30% at 70° C. for 60 minutes;

(h) sensitivity to enzymes: not inactivated by deoxyribonuclease; not inactivated by ribonuclease; not inactivated by glycosidase; but inactivated by protease;

(i) flow cytometry analysis: to concentrate cell division cycle of human leukemia cells to $G_0/G_1$ phase.

In accordance with the present invention, there is also provided a process for the production of the proteinaceous biological response modifier comprising: culturing human leukemia cells in a differentiation medium in the presence of a substance capable of inducing the human leukemia cells to differentiate into macrophage-like cells; separating the macrophage-like cells from the differentiation medium; activating the macrophage-like cells in a production medium by a mitogen to enhance the production of the proteinaceous biological response modifier; and isolating the proteinaceous biological response modifier from the production medium.

Preferably, prior to culturing human leukemia cells in the differentiation medium, the cells are proliferated by culturing them in a proliferation medium.

DESCRIPTION OF THE PREFERRED EMBODIMENTS

The human differentiation and activation factor (DAF) according to the present invention is produced by human macrophage-like cells, and is capable of at least inducing human leukemia cells to differentiate into terminally differentiated functionally matured cells, resulting in inhibition of cell growth of the cells, and finally for the leukemia cells to die in vitro. According to a process of the present invention, a large amount of DAF can be produced by culturing a large amount of cells in an industrial cell culturing apparatus.

Assay Method

The DAF of the present invention was quantitatively analyzed by an in vitro assay method established by the inventors, wherein the extent of the differentiation-induction of human monocytic leukemia cell line THP-1 into macrophage-like cells was measured. A sample is diluted until it becomes two-fold of the volume, step by step, with a culture medium. Each 0.1 ml of a series of the diluted samples is added into each well of a flat bottom type microplate (Falcon). THP-1 cells are cultured for 2 days in RPMI-1640 medium supplemented with 10% of fetal calf serum (FCS), at a temperature of 37° C.±0.5° C. in an incubator conditioned to a 5% carbon dioxide concentration (5% $CO_2$-incubator).

The cultured THP-1 cells are then washed with a phosphate buffer saline which is $Ca^{++}$ and $Mg^{++}$ free [PBS(-)] and suspended in RPMI-1640 medium supplemented with 5% of FCS to a concentration of $2 \times 10^5$ cells/ml. Then 0.1 ml of the suspension is added to the each well of the microplate and cultured at 37° C. in the 5% $CO_2$-incubator for 48 hours. After cultivation, suspended cells are removed from the well, leaving the cells adhered to the bottom of the well. The microplate is rinsed twice with PBS(-) gently, and 0.1 ml of 0.5% gentian violet staining solution is then added to each well to stain the adhered cells. The microplate is thoroughly washed with tap water to remove excess dye, and dried after decanting the water. 0.1 ml of 2-methoxyethanol is added to each well of the microplate to extract the dye from the cells. After about one hour the difference between absorbance at 550 nm and 414 nm of the extract is measured by a double beam method using Titertek Multiskan (Flow Laboratories, U.S.A.). The absorptions for the samples are compensated by the absorptions for the controls.

The absorption corresponds to the number of macrophage-like cells adhered to the bottom of each well of the microplate.

The activity of DAF in a diluted sample providing an absorption of 0.1 is defined as one unit/ml. For example, if a diluted sample prepared by dilution of an original sample to a 32-fold volume provides an absorption of 0.1, the activity of the original sample is 32 units/ml.

Properties of DAF (a) Molecular weight: 35,000 to 65,000.

The molecular weight was determined by fractionating a sample by gel filtration with Sephadex G-100 equilibrated with Dulbecco's phosphate buffer solution (0.2 g/l potassium chloride, 0.2 g/ml potassium dihydrophosphate, 8 g/l sodium chloride, 1.15 g/l disodium phosphate, pH 7.4), and comparing the DAF active band with standard proteins having a known molecular weight.

(b) Isoelectric point: 5.0 to 6.1.

The isoelectric point was determined by fractionating a sample by isoelectric chromatography according to a chromatofocusing method using a poly buffer exchanger (Pharmacia) and identifying the DAF active band.

(c) Physiological action on human leukemia cells: to induce human leukemia cells to differentiate into macrophage-like cells.

Human monocyte leukemia cells (THP-1) were cultured in the RPMI-1640 medium containing 10% FCS at 37° C. in the 5% $CO_2$-incubation, the cultured cells were washed throughout with PBS(-), and the washed cells were suspended in the RPMI-1640 medium containing 5% FCS to the concentration of $2 \times 10^5$ cells/ml medium. 0.5 ml of the suspension was added to each well of a 24 well flat bottom type cell culture plate (Falcon), 0.1 ml of the DAF sample and the same amount of the control solution were added to different wells and the cells were cultured in the 5% $CO_2$-incubation at 37° C. for 4 days.

Human promyelocytic leukemia cells (HL-60) were also cultured in the same manner as described above.

Table 1 shows the degree of cell growth of the human leukemia cells. The addition of DAF caused the human leukemia cells to be induced to differentiate into macrophage-like cells, resulting in inhibition of cell growth of the cells. Conversely the human leukemia cells not treated with DAF were myeloblast-like and showed a higher cell concentration.

TABLE 1

| Strain of human leukemia cell | Observation | Presence of DAF | Absence of DAF |
|---|---|---|---|
| THP-1 | Number of cells | $2.1 \times 10^5$ cells/ml | $10.7 \times 10^5$ cells/ml |
|  | Morphology | Macrophage-like cells | Myeloblast-like cells |
| HL-60 | Number of cells | $3.4 \times 10^5$ cells/ml | $17.7 \times 10^5$ cells/ml |
|  | Morphology | Macrophage-like cells | Myeloblast-like cells |

After culturing for 4 days, the properties of the human leukemia cells were tested. In the presence of DAF the human leukemia cells differentiated to macrophage-like cells in biological property as shown in Table 2.

TABLE 2

| Strain of human leukemia cells | DAF | Phagocytosis of latex beads | Candidacidal activity | NBT-reducing activity | Adhesion to vessel | Acid phosphatase | β-glu-curonidase |
|---|---|---|---|---|---|---|---|
| THP-1 | Presence | ++++ | +++ | +++ | ++++ | +++ | ++ |
|  | Absence | ± | − | ± | − | + | + |
| HL-60 | Presence | ++++ | ++ | +++ | ++++ | +++ | ++ |
|  | Absence | ± | − | ± | − | + | + |

Symbols −, ±, + to ++++ show the degree of activity or ability.

The above-mentioned properties, i.e., phagocytosis of polystyrene latex beads, candidacidal activity, adhesion to vessel, nitroblue tetrazolium dye (NBT) reducing activity, acid phosphatase activity and β-glucuronidase activity are used as characteristics for the identification of macrophages, as described in, for example, *Manual of Macrophage Methodology*, Marcel Dekker Inc. New York, 1981.

Figure 1:
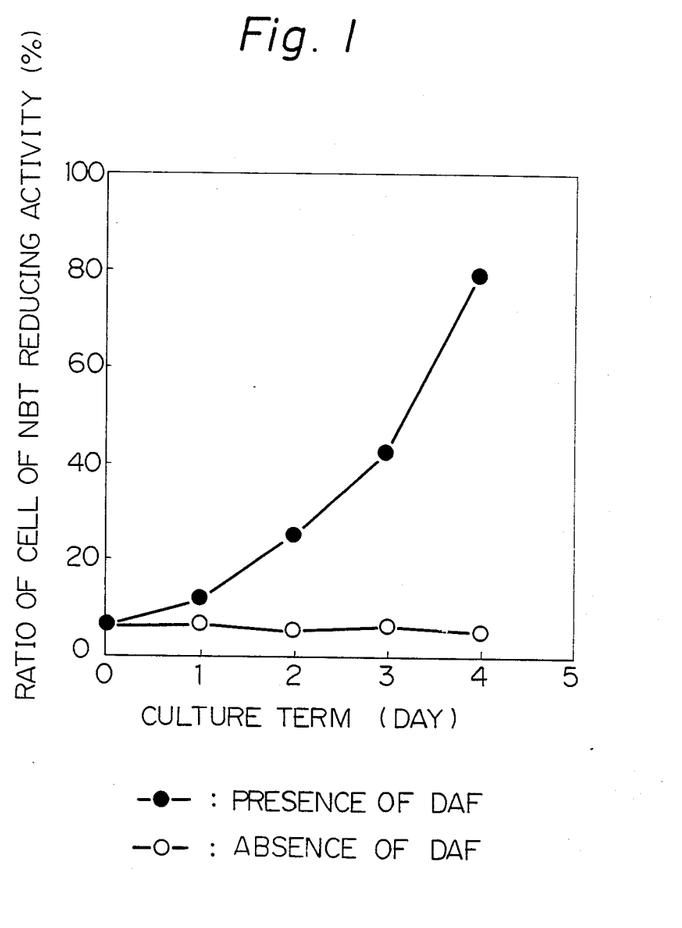
FIG. 1 is a graph showing the relationship between nitroblue tetrazolium dye (NBT) reducing activity provided by human leukemia cells treated with the DAF of the present invention and the culture term.
Figure 2:
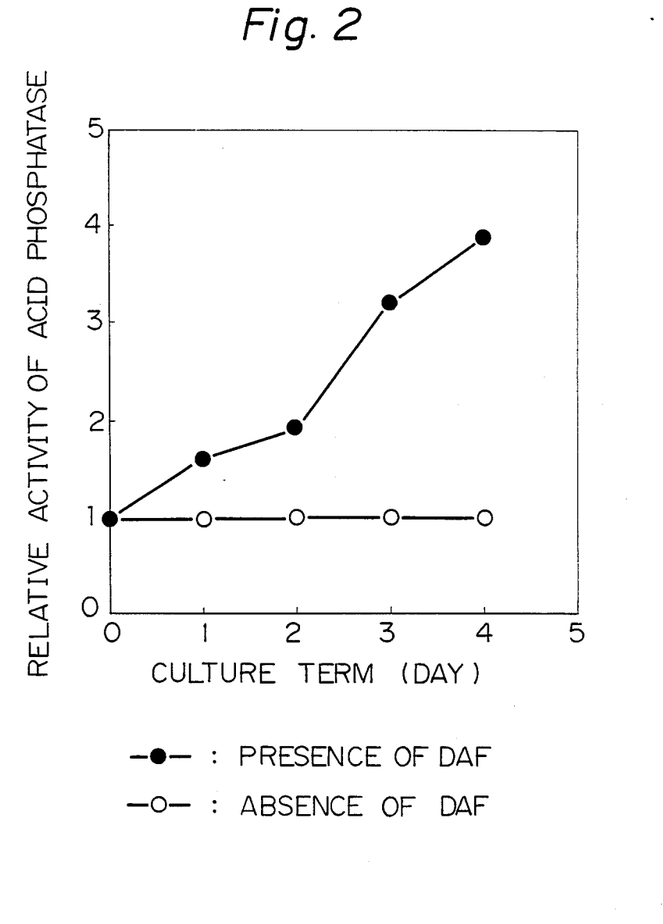
FIG. 2 is a graph showing the relationship between acid phosphatase activity provided by human leukemia cells treated with DAF and the culture term.

Comparisons between cells (THP-1) treated with DAF and cells (THP-1) not treated with DAF for NBT reducing activity and acid phosphatase activity are shown in FIGS. 1 and 2, respectively. As shown in the figures, the NBT reducing activity and the acid phosphatase activity increase with the time elapsed for the treated cells, but do not increase for the not treated cells.

(d) Physiological action on myeloid leukemia cells from mice: to induce myeloid leukemia cells from mice to differentiate into macrophage-like cells.

Myeloid leukemia cells M-1 from mice [*J. Cell Physiol.* 74,223 (1969)] were prepared by being cultured in the RPMI-1640 medium supplemented with 10% of horse serum for 3 days, and the cells were then suspended in the RPMI-1640 medium supplemented with 5% of horse serum to the concentration of $2 \times 10^5$ cells/ml.

The same tests were carried out as in the preceding paragraph (c), and showed the results as set forth in Table 3. The M-1 cells were induced to differentiate into macrophage-like cells in the presence of DAF, but were not induced in the absence of DAF.

TABLE 3

| DAF | Cell number (cells/ml) | Morphology | Phagocytosis of latex beads | NBT-reducing activity | Adhesion to vessel | Acid phosphatase | β-glu-curonidase activity |
|---|---|---|---|---|---|---|---|
| Presence | $4.4 \times 10^5$ | Macrophage-like cells | ++++ | +++ | +++ | ++ | +++ |
| Absence | $23.5 \times 10^5$ | Myeloblast-like cells | − | ± | − | + | + |

Culture for 4 days
Symbols −, ±, + to ++++ show the degree of activity or ability.

Figure 3:
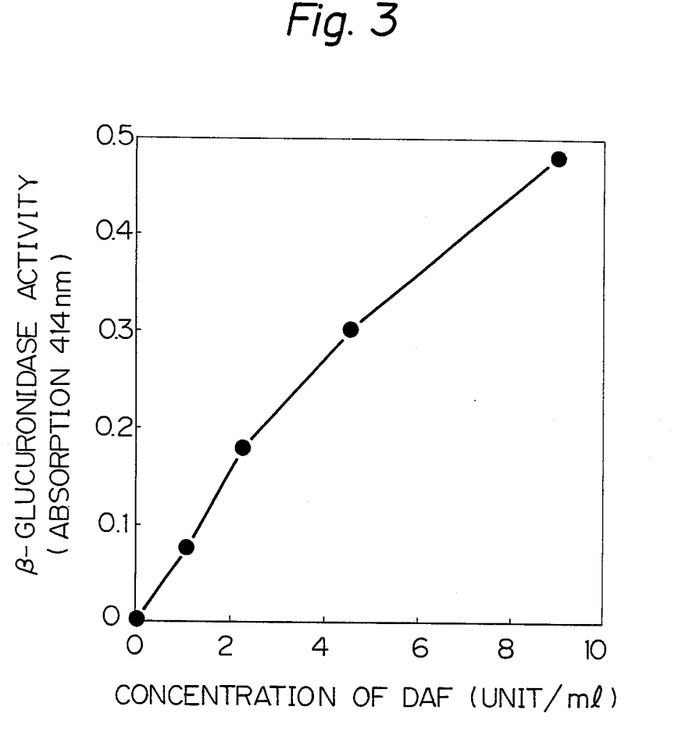
FIG. 3 is a graph showing the relationship between $\beta$-glucuronidase activity provided by myeloid leukemia cells from mice treated with the DAF, and the concentration of the DAF used.

FIG. 3 shows the amount of increase of β-glucuronidase activity produced by macrophage-like cells derived from the M-1 cells when the M-1 cells were cultured in the presence of DAF for 4 days.

Other properties of DAF of the present invention are described as follows:

(1) When a PBS(-) solution containing DAF (173 units/ml) was added to a column of concanavalin A-Sepharose (Pharmacia) and the column was washed with PBS(-), the DAF was not adsorbed on the concanavalin A-Sepharose and passed through with the PBS(-).

(2) When a PBS(-) solution containing DAF (173 units/ml) was added to a column of BlueSepharose CL-6B (Pharmacia) and the column was washed with PBS(-), the DAF was not adsorbed on the BlueSepharose CL-6B and passed through with the PBS(-).

(3) The pH-stability and thermostability were tested. DAF was dissolved in the buffer solutions as set forth in Table 4, the solutions were allowed to stand at 2° C. for 6 hours, neutralized to pH 7.4, and the residual activity of the DAF was measured.

In addition, DAF was diluted in a phosphate buffer solution of pH 7.4 and the solutions were heated under different conditions. The results are shown in Tables 4 and 5.

TABLE 4

| pH | Buffer solution | Residual activity (%) |
|---|---|---|
| 2.10 | Citrate buffer | 104 |
| 4.08 | Citrate-phosphate buffer | 96 |
| 6.09 | Citrate-phosphate buffer | 102 |
| 7.40 | Phosphate buffer | 100 |
| 7.98 | Tris-HCl buffer | 91 |
| 10.22 | Carbonate buffer | 84 |

TABLE 5

| Temperature (°C.) | Time (minutes) | Residual activity (%) |
|---|---|---|
| 56 | 60 | 83 |

TABLE 5-continued

| Temperature (°C.) | Time (minutes) | Residual activity (%) |
|---|---|---|
| 70 | 15 | 94 |
| 70 | 60 | 70 |
| 96 | 3 | 91 |

(4) Sensitivity to enzymes was measured according to a conventional method in which DAF was diluted in the buffer solutions as set forth in Table 6, subjected to the action of protease, nucleases or glycosidase and the residual activity of the DAF was measured. The results are shown in Table 6.

TABLE 6

| Enzyme | Buffer solution | Residual activity (%) |
|---|---|---|
| DNase (Deoxyribonuclease I) | Tris-HCl buffer pH 7.5 | 99 |
| RNase (Ribonuclease A) | Tris-HCl buffer pH 7.5 | 95 |
| Glycosidase (Neuraminidase) | Sodium acetate buffer pH 5.0 | 96 |
| Protease (Pronase E) | Phosphate buffer pH 7.4 | not more than 6 |

Figure 4:
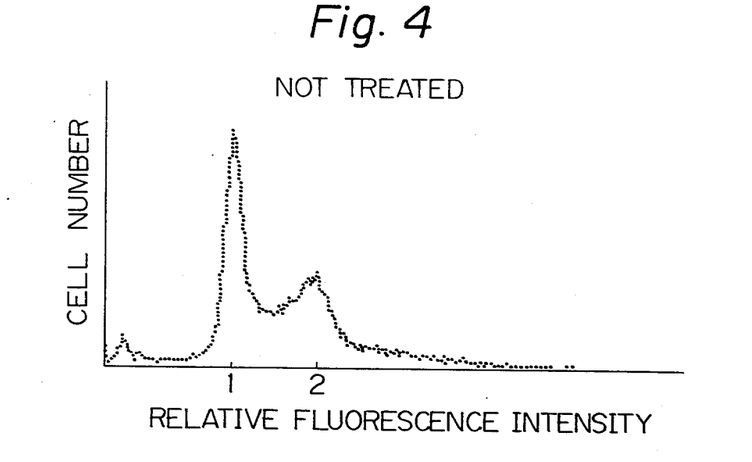
FIG. 4 is a chart obtained by cell cycle analysis with a cell sorter system of human leukemia cells not treated with the DAF.
Figure 5:
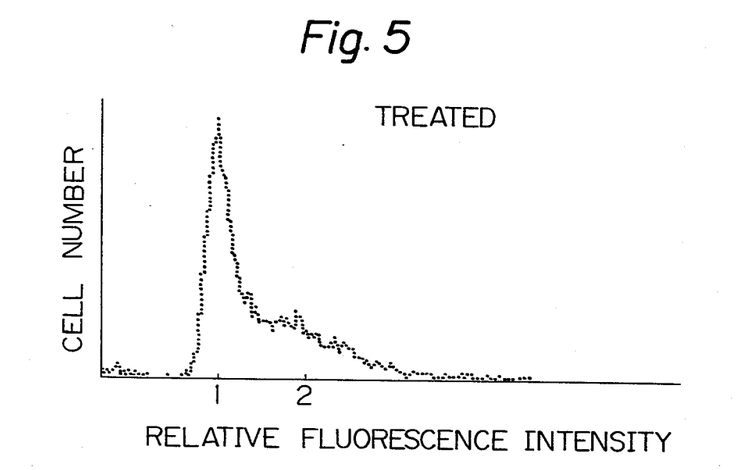
FIG. 5 is a chart obtained by cell cycle analysis with a cell sorter system of human leukemia cells treated with the DAF.

(5) The effect of DAF on the cell division cycle was tested by flow cytometry. DAF was diluted into the RPMI-1640 medium supplemented with 5% FCS to the concentration of 85 units/ml. Human monocytic leukemia cells were cultured in the medium prepared as above at 37° C. for 3 days in the 5% $CO_2$-incubator. Nuclei in the cells were stained with acrydineorange dye, and analysed with a cell sorter system (Coulter Electronics). The DAF concentrated cell division phase to $G_0/G_1$ phase as shown in FIG. 4. The detailed analysis method is described in, for example, *Proc. Natl. Acad. Sci.*, 73, 2881 (1976).

Process for Production of DAF

The process for the production of DAF according to the present invention comprises four steps, i.e., (i) a differentiation step where human leukemia cells are cultured in a differentiation medium in the presence of an inducer, to differentiate into macrophage-like cells; (ii) a separation step where the macrophage-like cells are separated from the differentiation medium; (iii) a production step where the macrophage-like cells are activated in a production medium by a mitogen to produce the target product DAF; and (iv) an isolation step where the DAF is isolated from the production medium.

Although not essential for the present invention, a proliferation step where the starting human leukemia cells are proliferated in a proliferation medium to obtain a large amount of human leukemia cells may be preferably carried out prior to the differentiation step.

(1) Human leukemia cells

In the process of the present invention any kind of human leukemia cells which can be induced to differentiate into macrophage-like cells by an inducer described hereinafter can be employed. Such cells include leukemia cell lines derived from human stock, primary culture isolated from a human having leukemia and its established cell lines, which can be induced to differentiate into macrophage-like cells. To obtain a large amount of industrial culture, established cell lines capable of vigorous growth may be preferably used. More specifically, human monocytic leukemia THP-1 cells [*International J. Cancer* 26, 171 (1980)], human promyelocytic leukemia HL-60 cells [*Nature,* 270, 347 (1977)], and human monocytic leukemia Mono-1 cells [*Virchows Arch. A. Path. Anal. and Histol.,* 371, 15 (1976)]etc., are preferably used.

(2) Proliferation step

As the proliferation medium, any medium which is usually employed for the culture of human cells can be utilized. Media including, for example, RPMI-1640 medium, Dulbecco's modified MEM medium, Eagle BME medium, Ham's medium, McCoy 5A medium, and Iscove's medium, etc., all of which are supplemented with about 0.5% to 20% of a serum such as fetal calf serum (FCS), newborn calf serum, calf serum and horse serum may be used. The compositions of such medium are described in *Manual for Cell Culture*, Kodan Sha, Japan, 1982. To prevent infection of the microorganisms, antibiotics such as 10 to 100 units/ml penicillin-G, 10 to 100 μg/ml streptomycin sulfate and 40 to 60 g/ml kanamycin sulfate may be added to the medium. Additionally, to promote proliferation of the cells, the medium may be supplemented with cell growth promoting substances such as amino acids, vitamins, proteins such as albumin and casein, insulin and transferrin. To control the pH value and adjust the concentration of carbonate anion in the medium, buffering agents such as 10 to 60 mM 4-(2-hydroxyethyl)-1-piperazinethansulphonate (HEPES) may be used.

For the culturing of the cells, any vessel which allows growth of the cells can be used.

When culturing the cells, human leukemia cells prepared as inoculum are suspended in the above-mentioned proliferation medium such as RPMI-1640 medium supplemented with 10% FCS to the cell concentration of about $1 \times 10^5$ to $5 \times 10^5$ cells/ml, preferably about $2 \times 10^5$ to $3 \times 10^5$ cells/ml, and the cells are cultured for 2 to 6 days, preferably 3 to 4 days, at a temperature of 35° to 38° C., preferably 37° C., in a 5% $CO_2$-incubator.

(3) Differentiation step

The cells proliferated in the proliferation step are collected by a conventional method such as centrifugation.

The cells thus obtained are then suspended in a differentiation medium. The differentiation medium is fundamentally the same as the proliferation medium, and a medium supplemented with 5% FCS is preferably used. The starting cell concentration is adjusted to typically about $3 \times 10^5$ to $30 \times 10^5$ cells/ml, preferably about $6 \times 10^5$ to $18 \times 10^5$ cells/ml.

To the suspension, a substance capable of inducing human leukemia cells to differentiate into macrophage-like cells, i.e., an inducer, is then added. As the inducer, phorbolesters such as 12-0-tetradecanoylphorbol-13-acetate (TPA), phorbol-12,13-dibenzoate (PDB), and phorbol-12,13-didecanoate (PDD); and diterpene compound mezerein (MEZ) are used. The structures and properties of these compounds are described in *Protein, Nucleic Acid and Enyzme*, Vol 24, 999 (1979). The concentration of the inducer added to the medium is typically about 0.005 to 5 μg/ml, preferably about 0.1 to 1 μg/ml.

Differentiation culturing is carried out for about 1 to 72 hours, preferably 8 to 36 hours, at a temperature of 35 to 38° C., preferably 37° C. Macrophage-like cells differentiated from leukemia cells will adhere to the surface of a culture vessel.

(4) Separation step

The macrophage-like cells thus formed are separated from the differentiation medium by a conventional method such as centrifugation or filtration. Then the collected cells are thoroughly washed with an appropriate buffer solution such as PBS(-) to remove the differentiation medium from the macrophage-like cells.

(5) Production step

In this step the macrophage-like cells are activated by a mitogen to enhance the production of DAF. Note, without activation of the mitogen, a lower level of DAF is produced.

The macrophage-like cells obtained in the separation step are then suspended in a production medium.

The production medium can be substantially the same as the proliferation medium but in order to ensure easy purification of the DAF in the next isolation step, it is preferred that the production medium does not contain serum. To enhance the production of the DAF, the production medium may contain, in addition, about 0.1 to 10 mg/ml of protein such as albumin obtained from a calf or human serum.

The mitogens which can be used as the activator include, for example, plant lectins and bacterial lipopolysaccharides. The lectins include succinylated concanavalin A, muramyldipeptide and phytohemagglutinin (Phaseolus vulgaris lectin). The bacterial lipopolysaccharides include those obtained from gram negative bacteria such as *Escherichia coli, Serratia marcescens* and *Salmonella typhimurium*. These mitogens are added to the medium in a concentration of typically about 1 to 50 μg/ml, preferably about 2 to 10 g/ml.

The production culturing is carried out at a temperature of about 35° C. to 38° C., preferably 37° C., for about 2 to 6 days to produce DAF in the cultured medium.

(6) Isolation step

The cultured medium thus obtained is treated by a conventional method such as centrifugation or filtration to remove the cells and obtain a supernatant containing DAF. From the supernatant the DAF is isolated and purified according to the conventional biochemical isolation procedures such as ultrafiltration, salting out for concentration, dialysis for desalting, gel filtration, electrophoresis, ion exchange chromatography or a combination thereof. For example, the supernatant is concentrated by ultrafiltration, and the concentrate is fractionated by gel filtration with Sephacryl S-200 or S-300, or Sephadex G-75, G-100 or G-150 (Pharmacia) to obtain active fractions. The combined active fraction is again concentrated by ultrafiltration, and the concentrate is fractionated with an anion exchanger such as DEAE-Sephadex, DEAE-Sepharose CL-6B or DEAE-Sephacel (Pharmacia) using a sodium chloride linear gradient elution method to obtain the active fraction. The combined active fraction is concentrated, desalted and lyophilized to obtain the product of this invention.

Anti-tumor activity of DAF

Tests were carried out to determine the anti-tumor activity of the DAF produced according to the above described process of the present invention.

Several kinds of human leukemia cells were inoculated into RPMI-1640 medium supplemented with 10% FCS to a cell concentration of $1.0 \times 10^5$ cells/ml. To the cell suspension a phosphate buffer solution containing 93 units/ml of DAF was added to the final concentration of 5 units/ml, and the cells were cultured at 37° C. for 4 days in a 5% $CO_2$-incubator.

After cultivation, the number of cells was counted with a Coulter counter (Coulter Electronics, U.S.A.) and the percent depression of leukemia cell growth was calculated. The results are shown in Table 7.

TABLE 7

| Human leukemia cells | Strain | Number of cells after 4 days | Percent depression |
|---|---|---|---|
| Human myelogenous leukemia cells | K-562 | $1.10 \times 10^5$ cells/ml | 0.65 |
| Human promyelocytic leukemia cells | HL-60 | 0.95 | −0.24 |
| Human monocytic leukemia cells | THP-1 | 0.89 | −0.76 |
| Human monocytic leukemia cells | Mono-1 | 1.05 | 0.42 |

$$\text{Percent depression} = \frac{\substack{\text{Cell number} \\ \text{after 4 days} \\ \text{in test} \\ \text{culture}} - \substack{\text{Cell number} \\ \text{at start} \\ \text{in test} \\ \text{culture}}}{\substack{\text{Cell number} \\ \text{after 4 days} \\ \text{in control} \\ \text{culture}} - \substack{\text{Cell number} \\ \text{at start} \\ \text{in control} \\ \text{culture}}} \times 100$$

From the above described results, the DAF of the present invention is expected to act as an anti-tumor pharmaceutical on the basis of its differentiation-induction ability. Such a type of anti-tumor agent is not known at present.

The following examples illustrate detailed embodiments of the present invention but in no way limit the invention.

EXAMPLE 1

A culture medium was prepared from RPMI-1640 medium powder by supplementing it with 10% of FCS (Flow), 50 units/ml of penicillin-G, 50 μg/ml of streptomycin sulfate and 50 μg/ml of kanamycin sulfate. Human monocytic leukemia cell line THP-1 cells were suspended in the medium to a cell concentration of $2 \times 10^5$ cells/ml, and 10 ml of the suspension was added to each of 3 plastic culture vessels having a diameter of 10 cm (Falcon). After culturing at 37° C.±0.5° C. in a 5% $CO_2$-incubation for 4 days, the cell concentration reached $12 \times 10^5$ cells/ml.

The cells were collected by centrifugation at 1000 rpm for 5 minutes, and resuspended in fresh RPMI-1640 medium supplemented with 5% of FCS to a cell concentration of $6 \times 10^5$ cells/ml, and 10 ml of the suspension was added to each of 6 plastic culture vessels having a diameter of 10 cm. To each culture vessel, 0, 0.01, 0.05, 0.1, 0.5, and 10 g/ml of TPA was added, and the cells were cultured to differentiate into macrophage-like cells for 20 hours at 37° C.±0.5° C. in a 5% $CO_2$-incubator.

The cells in each vessel were separately collected by centrifugation, thoroughly washed with PBS(-), and resuspended in 10 ml of RPMI-1640 medium supplemented with 5% of FSC.

To each suspension was added 20 μg/ml of succinylated concanavalin A obtained from jack beans (E.Y. Laboratories) and the suspension was cultured at 37° C.±0.5° C. in a 5% $CO_2$-incubator for 4 days. The cultured cell suspension was then centrifuged to remove the cells. The obtained supernatant was subjected to an in vitro assay for DAF. The results are shown in Table 8.

TABLE 8

| Concentration of TPA μg/ml | DAF produced units/ml |
|---|---|
| 0 | 4 |
| 0.01 | 52 |
| 0.05 | 70 |
| 0.1 | 85 |
| 0.5 | 103 |
| 1.0 | 120 |

EXAMPLE 2

The same procedure for the cell proliferation step as in Example 1 was repeated to obtain THP-1 cells.

For the differentiation step, the cells thus obtained were suspended in 350 ml of RPMI-1640 medium supplemented with 5% of FCS to a cell concentration of $6 \times 10^5$ cells/ml. The cell suspension was fractioned to to 10 plastic culture vessels having a diameter of 15 cm (Falcon), and differentiation culturing was carried out by adding 0.2 μg/ml of TPA to each vessel.

The cells were collected by centrifugation, washed with PBS(-), and production culturing was carried out in the same manner as in Example 1 for 4 days.

The cultured medium was centrifuged to remove the cells, and 345 ml of a supernatant containing DAF was obtained. The supernatant was desalted with an ultrafilter (Millipore) and subjected to ion exchange chromatography with DEAE-Sepharose CL-6B (Pharmacia) equilibrated with a 10 mM HEPES buffer solution and using a 0 to 0.6 M sodium chloride concentration gradient elution to obtain active fractions. The combined active fractions were again desalted with an ultrafilter, subjected to gel filtration with Sephacryl S-200 (Pharmacia) equilibrated with pH 7.4 PBS(-) using PBS(-) as an eluent to obtain active fractions. The obtained fractions were measured for DAF activity. The active fractions showing a molecular weight of 35,000 to 65,000 were combined and concentrated with an ultrafilter to obtain 13 ml of the product containing 3,350 units of DAF according to this invention.

EXAMPLE 3

The same procedure for the cell proliferation step as in Example 1 was repeated to obtain THP-1 cells.

For the differentiation step, the cells thus obtained were suspended in RPMI-1640 medium supplemented with 5% of FCS to a cell concentration of $6 \times 10^5$ cells/ml, and 10 ml of the cell suspension was put into each of 8 plastic culture vessels having a diameter of 10 cm. The differentiation culturing was carried out by adding the phorbol esters or mezerein as set forth in Table 9 to each vessel and culturing the cells for 24 hours.

The production culturing was carried out in the same manner as in Example 1, using 20 μg/ml of succinylated concanavalin A. The supernatant obtained by centrifugation was subjected to an in vitro assay for DAF and the results shown in Table 9 were obtained.

TABLE 9

| Differentiation Inducer | Concentration of inducer (μg/ml) | DAF produced (units/ml) |
|---|---|---|
| TPA | 0.05 | 77 |
|  | 0.5 | 115 |
| PDB | 0.05 | 25 |
|  | 0.5 | 153 |
| PDD | 0.05 | 58 |
|  | 0.5 | 89 |
| MEZ | 0.05 | 111 |
|  | 0.5 | 356 |

EXAMPLE 4

The same procedure for the cell proliferation step as in Example 1 was repeated to obtain the cells. For the differentiation step, the cells thus obtained were suspended in an Eagle's BME medium supplemented with 5% of FCS to a cell concentration of $8 \times 10^5$ cells/ml, and 30 ml of the suspension was put into a plastic culture vessel having a diameter of 15 cm. The differentiation culturing was carried out by adding 0.1 μg/ml of TPA to the vessel for 24 hours at 37° C. in a 5% $CO_2$-incubator.

For the production culturing, the cells were collected by centrifugation, thoroughly washed with PBS(-), resuspended in the Eagle's BME medium supplemented with 1 mg/ml of calf serum albumin, and 10 ml of the suspension was put into each of 3 plastic culture vessels having a diameter of 10 cm. After the addition of 5 μg/ml of lipopolysaccharide obtained from the gram negative bacteria as set forth in Table 10 to the suspensions, the production culturing was carried out at 37° C. for 5 days in a 5% $CO_2$-incubator. The cultured media were centrifuged to remove the cells. The supernatants were subjected to an in vitro assay for DAF. The results are shown in Table 10.

TABLE 10

| Origin of lipopolysaccharide | DAF produced (units/ml) |
|---|---|
| *Escherichia coli* | 173 |
| *Serratia marcescens* | 181 |
| *Salmonella typhimurium* | 154 |

EXAMPLE 5

The same procedure for the cell proliferation step as in Example 1 was repeated to obtain the THP-1 cells.

For the differentiation culturing, the cells thus obtained were suspended in RPMI-1640 medium supplemented with 5% of horse serum to a cell concentration of $8 \times 10^5$ cells/ml. Then 0.2 μg/ml of TPA was added to the suspension, and 10 ml of the suspension was put into each of 4 plastic culture vessels having a diameter of 10 cm. The differentiation culturing was carried out at 37° C. for 24 hours in a 5% $CO_2$-incubator.

For the production culturing, cells in each vessel were separately collected, washed with PBS(-) and resuspended in 10 ml of RPMI-1640 supplemented with 1% of horse serum. To these suspensions the plant lectins and muramyldipeptide as set forth in Table 11 were added, and the production culturing was carried out at 37° C. for 4 days in a 5% $CO_2$-incubator. The cultured media were centrifuged to remove the cells, and the supernatants obtained were subjected to an in vitro assay for DAF. The results are shown in Table 11.

TABLE 11

| Lectin | Concentration of lectin (μg/ml) | DAF produced (units/ml) |
| --- | --- | --- |
| Succinylated concanavalin A | 20 | 98 |
| Phytohemagglutinin | 20 | 79 |
| Muramyldipeptide | 20 | 95 |
| Not added | — | 28 |

EXAMPLE 6

For the proliferation culturing, 150 ml of a medium having the composition as the one used in Example 1 was prepared in a 500 ml spinner flask (Bellco). Human promyelocytic leukemia cell line HL-60 cells were inoculated into the above-mentioned medium to a cell concentration of $2 \times 10^5$ cells/ml, and the flask was sealed. The cells were cultured at 37° C. for 4 days with gentle stirring.

For the differentiation culturing, the cultured cells were collected by centrifugation, suspended in fresh RPMI-1690 medium to a cell concentration of $12 \times 10^5$ cells/ml, and 150 ml of the suspension was returned to the 500 ml spinner flask. Then 0.2 μg/ml of mezerein was added to the flask which was then sealed. The differentiation culturing was carried out at 37° C. for 20 hours with gentle stirring.

For the production culturing, the cells were collected by centrifugation, thoroughly washed with PBS(-) and resuspended in 150 ml of RPMI-1640 supplemented with 1 mg/ml of calf serum albumin, and simultaneously 10 μg/ml of succinylated concanavalin A was added to the suspension. The spinner flask containing the above described suspension was sealed, and the production culturing was carried out at 37° C. for 4 days with gentle stirring. The medium cultured in the spinner flask contained 12,250 units of DAF activity.

EXAMPLE 7

The cell proliferation culturing was carried out for 4 days in the same manner as in Example 1 to obtain human monocytic leukemia cell line Mono-1 cells.

For the differentiation culturing, the cells were suspended in fresh RPMI-1640 supplemented with 5% FCS to a cell concentration of $8 \times 10^5$ cells/ml. Then 30 ml of the suspension was put into each of 2 plastic culture vessels having a diameter of 15 cm, and 0.5 μg/ml of TPA was added to each vessel, and the differentiation culturing was carried out at 37° C. for 36 hours.

For the production culturing, the cells in the each vessel were separately collected and resuspended in fresh RPMI-1640 medium. 10 μg/ml of phytohemagglutinin was added to the vessel, and 5 μg/ml of lipopolysaccharide obtained from E. coli was added to another vessel. The production culturing was carried out at 37° C. for 3 days in a 5% $CO_2$-incubator. The cultured media were centrifuged to remove the cells, and the obtained supernatants were assayed for DAF activity. As a result, the culture added with phytohemagglutinin provided 31 units/ml of DAF activity and the culture added with lipopolysaccharide provided 15 units/ml of DA activity.

We claim:

1. A process for the production of a proteinaceous biological response modifier capable of inducing myeloid leukemia cells to differentiate into macrophage-like cells and which has the following properties:
   (a) molecular weight: 35,000 to 65,000;
   (b) isoelectric point: 5.0 to 6.1;
   (c) affinity to Concanavalin A Sepharose: not adsorbed;
   (d) affinity to Blue Sepharose resin: not adsorbed; and
   (e) pH-stability and thermostability: substantially not inactivated at pH 2 to 10, at 2° C. for 6 hours; not inactivated at 56° C. for 60 minutes; but inactivated by 30% at 70° C. for 60 minutes which comprises:
   culturing human leukemia cells in a differentiation medium in the presence of a substance capable of inducing the human leukemia cells to differentiate into macrophage-like cells;
   separating the macrophage-like cells from the differentiation medium;
   activating the macrophage-like cells in a production medium by a mitogen to enhance the production of the proteinaceous biological response modifier; and
   isolating the proteinaceous biological response modifier from the production medium which consists essentially of said proteinaceous biological response modifier.

2. A process according to claim 1, wherein the human leukemia cells are selected from the group consisting of human monocytic leukemia THP-1 cells, human promyelocytic leukemia HL-60 cells and human monocytic leukemia Mono-1 cells.

3. A process according to claim 1, wherein the substance capable of inducing the human leukemia cells to differentiate into macrophage-like cells is selected from the group consisting of 12-O-tetradecanoylphorbol13-acetate, phorbol-12,13-dibenzoate, phorbol-12,13didecanoate and mezerein.

4. A process according to claim 1, wherein the mitogen is a lectin selected from the group consisting of a lectin and a bacterial lipopolysaccharide.

5. A process according to claim 4, wherein the lectin mitogen is a selected from the group consisting of succinylated concanavalin A, phytohemagglutinin, and muramyldipeptide.

6. A process according to claim 4, wherein the mitogen is a bacterial lipopolysaacharide derived from a gram negative bacteria selected from the group consisting of Escherichia coli, Serratia marcescens and Salmonella typhimurium.

7. A process according to claim 1, wherein the differentiation medium and production medium are selected from the group consisting of RPMI-1640 medium, Dulbecco's modified MEM medium, Eagle's BME medium, Ham's medium, McCoy 5A medium and Iscove's medium.

8. A process according to claim 1, wherein prior to cultivating the human leukemia cells in the differentiation medium, the human leukemia cells are proliferated in a proliferation medium.

9. A composition consisting essentially of a purified and isolated proteinaceous biological response modifier capable of inducing myeloid leukemia cells to differentiate into macrophage-like cells, which is inductively produced by culturing human leukemia cells in the presence of a substance capable of inducing the human leukemia cells to differentiate into macrophage-like cells, and activating the macrophage-like cells by a mitogen and having the following properties:
   (a) molecular weight: 35,000 to 65,000;

(b) isoelectric point: 5.0 to 6.1;
(c) affinity to Concanavalin A Sepharose: not adsorbed;
(d) affinity of Blue Sepharose resin: not adsorbed; and
(e) pH-stability and thermostability: substantially not inactivated at pH 2 to 10, at 2° C. for 6 hours; not inactivated at 56° C. for 60 minutes; but inactivated by 30% at 70° C. for 60 minutes.

10. A composition according to claim 9, which is produced by culturing human monocytic leukemia THP-1 cells in the presence of a substance capable of inducing said THP-1 cells to differentiate into macrophage-like cells, activating the macrophage-like cells by a mitogen to enhance the production of said proteinaceous biological response modifier and isolating said proteinaceous biological response modifier.

11. A composition according to claim 9, which is produced by culturing human promyelocytic leukemia HL-60 cells in the presence of a substance capable of inducing said promyelocytic leukemia HL-60 cells to differentiate into macrophage-like cells, activating the macrophage-like cells by a mitogen to enhance the production of said proteinaceous biological response modifier.

12. A composition according to claim 9, which is produced by culturing human monocytic leukemia Mono-1 cells in the presence of a substance capable of inducing said monocytic leukemia Mono-1 cells to differentiate into macrophage-like cells, activating the macrophage-like cells by a mitogen to enhance the production of said proteinaceous biological response modifier and isolating said proteinaceous biological response modifier.

13. A composition according to claim 9, which is lyophilized.

14. A composition according to claim 9, which is in the form of a solution.

15. A composition according to claim 14, which comprises 3,350 units of said biological response modifier in 13 ml of said solution.

* * * * *